United States Patent [19]

Eddy et al.

[11] Patent Number: 4,542,226

[45] Date of Patent: Sep. 17, 1985

[54] METHOD FOR MAKING SILOXANENORBORNANE BISANHYDRIDE

[75] Inventors: Victoria J. Eddy, Schenectady; John E. Hallgren, Scotia, both of N.Y.

[73] Assignee: General Electric Company, Schenectady, N.Y.

[21] Appl. No.: 631,421

[22] Filed: Jul. 16, 1984

[51] Int. Cl.[4] .............................. C07F 7/18; C07F 7/20
[52] U.S. Cl. ..................................................... 549/214
[58] Field of Search .......................................... 549/214

[56] References Cited

U.S. PATENT DOCUMENTS 4,381,396 4/1983 Ryang ................................. 549/234

Primary Examiner—Norma S. Milestone
Attorney, Agent, or Firm—William A. Teoli; James C. Davis, Jr.; James Magee, Jr.

[57] ABSTRACT

A method is provided for making siloxanenorbornane bisanhydride. Norbornane anhydride is initially hydrosilylated with dimethylchlorosilane in the presence of a platinum catalyst. The resulting dimethylchlorosilyl norbornane anhydride is thereafter hydrolyzed while in the molten state.

3 Claims, No Drawings

METHOD FOR MAKING SILOXANENORBORNANE BISANHYDRIDE

BACKGROUND OF THE INVENTION

Prior to the present invention as shown by Ryang U.S. Pat. No. 4,381,396 assigned to the same assignee as the present invention, silylnorbornane anhydrides were made by reacting 5-norbornene-2,3-dicarboxylic anhydride or "norbornene anhydride" with a silane such as dimethylchlorosilane and an organic solvent, for example, toluene in the presence of a platinum catalyst. The mixture was then subjected to a vacuum stripping operation to remove volatiles. The resulting diorganohalosilylnorbornane 2,3-dicarboxylic anhydride, such as 5-dimethylchlorosilyl-norbornane-2,3-dicarboxylic anhydride was then hydrolyzed in water at 0° C. in an organic solvent, such as tetrahydrofuran. The hydrolysis product was then stripped by heating to an elevated temperature, such as 200° C. under reduced pressure. There was obtained an 80% yield of 5,5'-(1,1,3,3-tetramethyl-1,1,1,3-disiloxanedialyl)-bis-norbornane-2,3-dicarboxylic anhydride having the formula

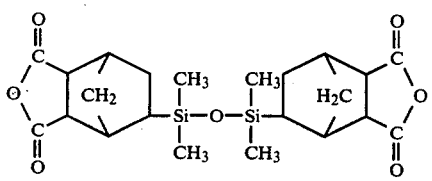

referred to hereinafter as "siloxane norbornane bisanhydride".

The present invention is based on discovery that siloxanenorbornane bisanhydride can be made by initially effecting a reaction between norbornene anhydride with dimethylchlorosilane in the presence of an effective amount of platinum catalyst and an organic solvent, followed by the vacuum distillation of the resulting mixture to produce 5-dimethylchlorosilyl-norbornane 2,3-dicarboxylic anhydride. Unexpectedly, the hydrolysis of this chlorosilyl-norbornane anhydride at a temperature of about 100°–180° C., while in the molten state, and its stripping under reduced pressure, has been found to provide siloxanenorbornane bisanhydride at yields exceeding 95%, such as 98%. Furthermore, the hydrolysis of the acid anhydride, a well known reaction, is not observed.

STATEMENT OF THE INVENTION

There is provided by the present invention, a method for making siloxanenorbornane bisanhydride which comprises, (1) hydrosilylating 5-norbornene-2,3-carboxylic anhydride with dimethylchlorosilane in the presence of an effective amount of a platinum catalyst and an organic solvent, (2) vacuum distilling the mixture of (1) to recover 5-dimethylchlorosilyl-norbornane-2,3-dicarboxylic anhydride, (3) hydrolyzing the 5-dimethylchlorosilyl-norbornane 2,3-dicarboxylic anhydride at a temperature in the range of from about 100°–180° C. and (4) stripping the mixture of (3) under reduced pressure.

In addition to providing the optimum yields of siloxanenorbornane bisanhydride, the method of the present invention also allows for the recovery of such bisanhydride free of residual catalysts and other impurities.

Experience has shown that the hydrosilylation reaction between 5-norbornene-2,3-dicarboxylic anhydride and dimethylchlorosilane can be facilitated in the presence of an inert organic solvent, for example, diglyme, toluene, chlorobenzene, ethyleneglycoldimethylether, tetrahydrofuran, etc. The platinum catalyst and the norbornene anhydride can be dissolved in organic solvent and warmed to a temperature of about 80° C. The solution can then be maintained at 70°–100° C. and the silane added at a rate sufficient to maintain a gentle reflux. Following complete reaction, the solvent can be removed by distillation and the product isolated and purified by vacuum distillation. For example, a pressure of about 0.05 to 1 torr.

The chlorosilyl norbornane can be warmed to a temperature of about 100°–110° C. and an excess of water can be added to the chlorosilane while in a molten state. After an hour, excess water can be removed under reduced pressure, to produce a colorless glassy solid. Purification of the glassy solid by tituration with ether or other suitable organic solvent will provide for the isolation of siloxanenorbornane bisanhydride, a white crystalline solid having a melting point of 125°–149° C. in quantitative yield.

Hydrosilylation catalysts which can be used in the practice of the present invention are, for example, platinum complexes of unsaturated siloxanes as shown by Karstedt U.S. Pat. No. 3,775,452, Ashby U.S. Pat. Nos. 3,159,601 and 3,159,662 and Lamoreaux U.S. Pat. No. 3,220,972 assigned to the same assignee as the present invention. An effective amount of a platinum catalyst is about 0.001%–0.1% by weight platinum, based on the weight of the hydrosilylation mixture.

The following example is given by way of illustration and not by way of limitation. All parts are by weight.

EXAMPLE

There was added 500 ppm of platinum as a 5% solution of a platinum complex of an unsaturated siloxane, as shown by Karstedt U.S. Pat. No. 3,775,452 to a mixture, while it was being stirred at 80° C., of 100 grams of 5-norbornene-2,3-dicarboxylic anhydride and 100 ml. of toluene. The norbornene anhydride toluene mixture had been dried by azeotropic distillation. There was then added dropwise to the resulting mixture, 64 grams of dimethylchlorosilane. The silane was added to the olefin slurry at a rate sufficient to maintain a gentle reflux at a pot temperature of 80° C. After the addition of the silane, which lasted about 1–2 hours, the mixture was maintained at 80° C. for an additional 4–6 hours. During the hydrosilylation of the norbornene anhydride, the mixture was stirred constantly. Upon completion of the addition reaction as shown by a disappearance of olefinic resonance by NMR, the mixture was cooled to room temperature. Solvent and other volatiles were removed at a pressure of about 60 torr. The resulting product was purified by distillation. It had a boiling point of 165°–170° C. (0.15 mm.). Based on the method of preparation, there was obtained 1-dimethylchlorosilyl-norbornane-3,4-dicarboxylic anhydride at a 95% yield. The product had a melting point of 105°–107° C.

There was added 6.2 ml. of water to 164.6 grams of molten 1-dimethylchlorosilyl-norbornane-3,4-dicarboxylic anhydride while it was stirred and heated in an oil bath 110°–115° C. After 1 hour, an additional 1 ml. of water was added and the stirring continued for a total of 2 hours. Excess water was then stripped in vacuo. There was obtained a hard glassy solid when the product was cooled to dry ice temperature. There was obtained 145.5 g of a finely divided white powder when the product was titurated with ether and dried in vacuo. This represented a yield of 98%. Based on method of preparation and its spectra, the product was 1,3-bis(1-norbornane-3,4-dicarboxylic anhydride)-1,1,3,3-tetramethyldisiloxane. The melting point of the product was 125°–148° C. The product was free of residual catalyst and other impurities such as norbornene anhydride as shown by gas and ion chromatography.

Although the above example is directed to only a few of the very many variables which can be employed in the practice of the present invention, it should be understood that the method of the present invention can utilize a much broader variety of organic solvents and conditions which are set forth in the description preceding this example.

What is claimed is:

1. A method for making silylnorbornane dianhydride of the formula

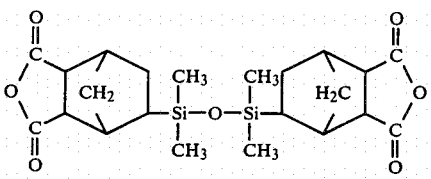

which comprises
   (1) hydrosilylating 5-norbornene-2,3-carboxylic anhydride with dimethylchlorosilane in the presence of an effective amount of a platinum catalyst and an organic solvent;
   (2) vacuum distilling the mixture of (1) to recover 5-dimethylchlorosilyl-norbornane-2,3-dicarboxylic anhydride;
   (3) hydrolyzing the 5-dimethylchlorosilyl-norbornane 2,3-dicarboxylic anhydride at a temperature in the range of from about 100°–180° C. and
   (4) stripping the mixture of (3) under reduced pressure.

2. A method in accordance with claim 1, where the solvent is toluene.

3. A method in accordance with claim 1, where the platinum catalyst is a platinum complex of an unsaturated siloxane.

* * * * *